United States Patent [19]

Oka et al.

[11] Patent Number: 4,724,210

[45] Date of Patent: * Feb. 9, 1988

[54] METHOD FOR PURIFICATION OF INFLUENZA VIRUS

[75] Inventors: Tetsuya Oka; Kunio Ohkuma, both of Kumamoto; Tetsuo Kawahara, Ohzu; Mitsuo Sakoh, Kumamoto, all of Japan

[73] Assignee: Juridical Foundation the Chemo-Sero-Therapeutic Research Institute, Kumamoto, Japan

[*] Notice: The portion of the term of this patent subsequent to May 7, 2002 has been disclaimed.

[21] Appl. No.: 764,128

[22] Filed: Aug. 9, 1985

[30] Foreign Application Priority Data

Aug. 9, 1984 [JP] Japan ................. 59-167324

[51] Int. Cl.$^4$ .................. C12N 7/02; C12N 7/00; A61K 39/12
[52] U.S. Cl. ................. 435/239; 435/235; 424/89
[58] Field of Search ............ 435/235, 803, 239; 424/89; 210/927; 530/412, 413

[56] References Cited

U.S. PATENT DOCUMENTS

| | | | |
|---|---|---|---|
| 3,422,187 | 1/1969 | Herzberg | 424/89 X |
| 3,547,779 | 12/1970 | Machlowitz | 424/89 X |
| 3,842,062 | 10/1974 | Eastman | 530/411 |
| 3,920,625 | 11/1975 | Andersson et al. | 530/382 |
| 4,138,287 | 2/1979 | Andersson et al. | 435/239 |
| 4,160,019 | 7/1979 | Bjorklund | 436/520 |
| 4,168,300 | 9/1979 | Andersson et al. | 436/514 |
| 4,181,713 | 1/1980 | McAleer et al. | 424/86 |
| 4,356,169 | 10/1982 | Simons et al. | 424/89 |
| 4,434,093 | 2/1984 | Zolton et al. | 252/626 |
| 4,515,714 | 5/1985 | Kawahara et al. | 530/380 |

OTHER PUBLICATIONS

Nilsson et al, "Immobilization of Enzymes and Affinity Ligands to Various Hydroxyl Group Carrying Supports Using Highly Reactive Sulfonyl Chlorides", Biochem. and Biophys. Research Comm., 102, (1): 449–457 (1981).

Einarsson et al, "A Two-Step Procedure for the Purification of Hepatitis B Surface Antigen (HBsAg)", Vox Sang: 41: 91–97 (1981).

Einarsson et al, "Purification of Hepatitis B Surface Antigen by Affinity Chromatography", Vox Sang, 35: 224–233 (1978).

Wilchek et al, "Structure of a Soluble Super-Active Insulin is Revealed by the Nature of the Complex Between Cyanogen-Bromide-Activated Sepharose and Amines", Proc. Nat. Acad. Sci. USA, 72, (3): 1055–1058 (1975).

Primary Examiner—Esther M. Kepplinger
Assistant Examiner—Shawn P. Foley
Attorney, Agent, or Firm—Fleit, Jacobson, Cohn & Price

[57] ABSTRACT

Disclosed is a method for the purification of an influenza virus, which comprises subjecting a solution containing the influenza virus to column chromatography using, as a gel for chromatography, a sulfuric acid ester of cellulose or a crosslinked polysaccharide. The method can provide highly purified influenza virus which is useful for obtaining an effective vaccine against influenza.

5 Claims, No Drawings

METHOD FOR PURIFICATION OF INFLUENZA VIRUS

BACKGROUND OF THE INVENTION

The present invention relates to a method for purification of influenza virus, and particularly to such method for obtaining effective vaccines against influenza.

Influenza is an infectious disease which rapidly spreads to lead to nation-wide or even world-wide prevalence. For example, there occured world-wide prevalences in 1918-1921 and in 1957. In the former case, there were reported patients of about 600 millions and deaths of exceeding 20 millions throughout the world, including about 24 millions of patients and 390 thousands of deaths in Japan. Statics figures in the past two decades in Japan shows that 0.3 to 8.5 patients per population of 100 thousands have died due to influenza. Taking into consideration the number of patients died from the complications, the mortality rate with influenza will be estimated to be much higher.

The only possible way to pevent such horrible prevalence of influenza is a vacination, in which there is used a vacine produced by purifying influenza virus. A typical conventional process for purifying influenza virus to produce an inluenza vaccine is conducted as follows:

Hens' eggs incubated for 11 days
↓
Inoculation of influenza virus into the eggs
↓
Propagation of the virus (33-35° C., 2 days)
↓
Cooling (2-5° C., overnight)
↓
Harvest of the allantoic fluid
↓
Centrifugation at a low speed
↓
Supernatant  Precipitate
↓
Chemical refining
↓
Refining by density-gradient centrifugation -continued ↓
Refined virus fluid
↓ ←— Addition of ether polysolvate
Ether treatment
↓
Water layer   Ether layer
↓
Removal of ether
↓
Removal of glyco-components
↓
Addition of stabilizer & preservative
↓
Filtration
↓
Single strain vaccine
↓
Final bulk As shown in the above, the conventional process requires sophisticated steps of purifying influenza virus, such as that contained in the allantoic fluid, by use of density-gradient centrifugation after carrying out refinment steps by low-speed centrifugation and chemical techniques. The refining of influenza virus by subjecting the allantoic fluid directly to the density-gradient centrifugation is not feasible since it will result in damage of the density-gradient liquid layer, Thus, the allantoic fluid containing the virus is pretreated by a chemical refining, generally with barium sulfate, by which the virus is purified by being adsorbed onto the surface of barium sulfate. However, such a prerefining technique with barium sulfate is troublesome in handling a large volume of fluid and entails difficulties in disposing of the barium sulfate after use. Other refining techniques, such as ultrafiltration or high-speed centrifugation, may be considered, but they are still troublesome and not suitable for handling a large amount of allantoic fluid.

In addition, the conventional method as mentioned above is not efficient in extracting immunologically active components of influenza virus. It is generally believed that, among the constituent elements of influenza virus, HA (Hemagglutinin) and NA (Neuraminidase), proteins both known as surface antigens, are the immunologically active components, with HA serving as an infection-preventing antigen and NA assisting in the prevention of infection when a vaccine is prepared from influenza virus. However, the conventional refining process simply removes lipids with ether, and a vaccine produced by such process still contains immunologically inactive or scarcely active proteins, nucleic acids, lipids and other substances, in addition to HA and NA which are generally contained in amounts of about 30% and about 2 to 3%, respectively, of the total proteins of influenza virus. The presence of the unessential substances in the vaccine may cause undesirable side effects when the vaccine is administered. Thus, such vaccine has to be administered in a restricted amount, which limits its immunological effectiveness.

SUMMARY OF THE INVENTION

It is therefore an object of the present invention to provide a method by which influenza virus can be purifred in a simple manner to produce a vaccine against influenza.

It is another object of the present invention to provide a method by which the immunological active components, known as the surface antigens of influenza virus, can be efficiently purified to permit the production of an effective and safe vaccine against influenza.

Other objects and features of the present invention will be apparent from the following descriptions.

The present invention is based on the discovery that a sulfuric acid ester of cellulose or a crosslinked polysaccharide has a specific affinity with influenza virus, not only with influenza virus as a whole but with the surface antigens (HA and NA proteins), and is effecitve for isolation and purification of such virus or virus proteins from a material containing the same. Thus, according to the present invention, there is provided a method for the purification of influenza virus which comprises subjecting a solution containing the influenza virus to column chromatography using, as a gel for chromatography, a sulfuric acid ester of a crosslinked polysaccharide or cellulose.

The sulfuric acid ester cellulose to be used in the present invention includes a sulfuric acid ester of crystalline cellulose or cellulose having crystalline area and non-crystalline area. These starting celluloses are commercially available, for example, as Abicel (manufactured by Asahi Kasei in Japan), Cellulofine GC-15, GC-100, or GC-200 (manufactured by Chisso Corp. in Japan).

The sulfuric acid ester of a crosslinked polysacharide to be used in the present invention includes a sulfuric acid ester of polysaccharide, such as dextran, cellulose, agarose, which is crossliked with a crosslinking agent, such as epichlorohydrin, dichlorohydrin, dibromohydrin, ethylene glycol bisepoxypropyl ether. The crosslinked polysaccharides are commercially available, for example, as crossliked dextran such as Sphadex G-10, G-25, G-50, and G-100 (manufactured by Pharmacia in Sweden), crosslinked agaroses such as Sepharose Cl-2B, Cl-4B, and Cl-6B (manufctured by Pharmacia in Sweden), and cross-liked celluloses such as Cellulofine GCL-25, GCL-90 (manufactued by Chisso Corp. in Japan).

The sulfation of such crosslinked polysaccharide or cellulose can be carried out by a conventional method. However, the gel for chromatography to be used in the present invention is charcterized in that it is prepared by directly sulfating cellulose or a crosslinked polysaccharide, saccharide, which are water-insoluble, with a sulfating gent such as chlorosulfonic acid or anhydrous sulfuric acid in an organic solvent (e.g. pyridine). Thus, the resultant gel is water-insoluble and highly stable. Further, such gel of the sulfuric acid ester of cellulose or a crosslinked polysaccharide exhibits an extremely high adsorbing activity since it is fully sulfated, even at the inner regions thereof. The use of the gel is also advantageous from an economical standpoint, because it can be easily prepared at a low cost. The degree of sulfation (content of the sulfonyl group) of crosslinked polysaccharide is usually in the range of 0.1 to 40%, preferably 10 to 40%, based on the weight of the crosslinked polysaccharide, and the degree of sulfation of cellulose is usually in the range of 0.1 to 5.0%, based on the cellulose.

The procedure of purification of influenza virus and/or the surface antigens (HA and NA proteins) by column chromatography using the sulfuric acid ester of a crosslinked polysaccharide or cellulose is carried out in a similar manner to that in the conventional column chromatography. For instance, the method is carried out in the following manner. First, a sulfuric ester of a crosslinked polysaccharide or cellulose (preferably, in the form of spherical particles) is packed within a column, which is equilibrated with a suitable buffer solution having an ionic strength of about 0.001 to 2.0, for example, 0.01M phosphate buffered saline solution (pH 7.4) and 0.1M sodium chloride-containing citrate buffer solution (pH 7.2). After the equilibration, a solution containing influenza virus to be treated is passed through the column in order to adsorb such virus onto the gel, followed by washing with the same buffer solution as used for the above equilibration. Thereafter, the adsorbed influenza virus is eluted from the column by passing through the column a suitable buffer solution having an ionic strength larger than that of the buffer solution used for the equilibration or the washing, for example, 1.0M or 1.5M sodium chloride-containing phosphate buffer solution (pH 6–9) to give desired highly purified influenza virus.

The method of the present invention can be conducted at any stage in the purification of influenza virus proteins. For example, the method of the present invention can be applied directly to an allantoic fluid or a culture broth infected with an influenza virus, so that the influenza virus as a whole can be specifically separated from the other substances contained in such fluid or liquid. The method of the present invention can also be applied to a solution which has undergone some purification process(es) beforehand, in order to further purify influenza virus. For example, a solution after the ether-treatment, which has been removed of lipids but may contain various proteins and nucleic acids as well as HA and NA proteins, can be subjected to the method of the present invention so as to specifically isolate the HA and NA proteins from the other substances contained in the solution. Of course, two or more of such purification procedures can be combined, optionally with conventional separation techniques (e.g. ultra-centrifugation or ion exchange chromatography), so as to obtain influenza virus purified as highly as possible, particularly, with respect to HA and NA proteins. It should also be noted that the present invention is applicable to a solution containing influenza virus of any type or any origin. Thus, the method of the present invention can be employed in purifying virus of type A or type B influenza as well as the other types of influenza. The starting influenza virus can be from animals, such as horses, pigs, chickens, turkeys or gulls, as well as from human beings. The method of the present invention may also be applied to a solution containig influenza virus proteins expressed by means of genetic engineering (e.g. Proc. Natl. Acad. Sci. USA, Vol.82, pp.2019-2023, April 1985, Biochemistry).

According to the purification method of the present invention, influenza virus can be purified to a high degree, i.e. to several to several tens times the purity thereof in the starting solution, and can be recovered at a high rate, because the sulfonyl group bonds directly to the crosslinked polysaccharide or cellulose in the sulfuric acid ester of a crosslinked polysaccharide or cellulose and hence it has a high content of sulfonyl group and shows excellent specific adsorbability to influenza virus. The purification method of the present invention can be easily carried out on an industrial scale without need for expensive equipment and give the desired purified influenza on an industrial scale with lower cost. Besides, the gel used therein is very stable, and the product thus obtained has no impurities as occasionally observed in the conventional products.

The present invention will now be illustrated by the following Preparations (preparations of gels for chromatography) and Examples, but should not be construed to be limited thereto.

PREPARATION 1

To pyridine (600 ml) is added dropwise chlorosulfonic acid (117 g) at below 0° C. After the addition, the mixture is heated to 65-70° C. To the mixture is added crystalline cellulose (Abicel for chromatography, manufactured by Asahi Kasei) (80 g), and the mixture is stirred at 65°-70° C. for 4 hours. After the completion of the reaction, the reaction mixture is cooled and then neutralized with 10% aqueous sodium hydroxide. The gel thus obtained is separated by filtration and washed well with 0.01M phosphate buffer-aqueous sodium chloride mixture to give a cellulose sulfate gel.

PREPARATION 2

To pyridine (600 ml) is added dropwise chlorosulfonic acid (117 g) at below 0° C. After the addition, the mixture is heated to 65°-70° C. To the mixture is added crystalline cellulose gel (Cellulofine GC-15, manufactured by Chisso Corp.) (80 g), and the mixture is stirred at 65°-70° C. for 3 hours. After the completion of the reaction, the mixture is cooled and neutralized with 10% aqueous sodium hydroxide. The gel thus obtained is separated by filtration and washed well with 0.01M phosphate buffer-aqueous sodium chloride mixture to give a cellulose sulfate gel.

PREPARATION 4

To pyridine (200 ml) is added dropwise chlorosulfonic acid (11 ml) at below 0° C. After the addition, the mixture is heated to 65°-70° C. To the mixture is added epichlorohydrin-crosslinked dextran (Sephadex G-50, manufactured by Pharmacia) (7.5 g), and the mixture is stirred at 65°-70° C. for 4 hours. After the reaction, the reaction mixture is cooled and then neutralized with aqueous sodium hydroxide. The gel thus obtained is separated by filtration and washed well with 0.01M phosphate-buffered saline solution to give a crosslinked dextran sulfate.

To a mixture (210 ml) of pyridine-chlorosulfonic acid prepared in the same manner as described in the above Preparation 3 is added dried product of crosslinked cellulose gel (Cellulofine GCL-25, manufactured by Chisso Corp.)(7.5 g), and the mixture is reacted at 65°-70° C. for 4 hours. After the reaction, the reaction mixture is cooled and neutralized with aqueous sodium hydroxide. The gel thus obtained is separated by filtration and washed well with 0.01M phosphate-buffered saline solurion to give a cross-linked cellulose sulfate (7.2 g).

PREPARATION 5

To a mixture (210 ml) of pyridine-chlorosulfonic acid prepared in the same manner as described in the above Preparation 3 is added crosslinked agarose gel (Sepharose CL-6B, manufactured by Pharmacia)(30 ml) which has been impregnated with pyridine, and the mixture is reacted at 65°-70° C. for 4 hours. After the reaction, the mixture is cooled and neutralized with aqueous sodium hydroxide. The gel thus obtained is separated by filtration and washed well with 0.01M phosphate-buffered saline solution to give a crosslinked agarose sulfate (23 ml).

EXAMPLE 1

The cellulose sulfate gel obtained in the manner as described in Preparation 2 is packed within a column (50 mm$\phi \times$170 mm), and the packed column is equilibrated with 0.01M phosphate-buffered saline solution (pH 7.4) containing 0.14M sodium chloride. Then, through the column is passed 4,200 ml of an allantoic fluid containing A/Philipine (H$_3$N$_2$) type influenza virus harvested from hen's eggs (incubated for 11 days) inoculated w th said virus and cultured for 48 hours at 34° C. The allantoic fluid has a virus content of 77 in terms of CCA (Chick cell agglutination), a protein nitrogen content of 377 $\mu$g/ml as determined by Lowry's method and a specific activity of 0.20 (virus content/protein nitrogen content). After the passage of the allantoic fluid, the column is washed with 2,500 ml of 0.01M phosphate buffer solution containg 0.19M sodium chloride. Then, the adsorbed material is eluted with 0.01M phosphate buffer solution containing 1.49M sodium chloride, to give an eluate of 170 ml. The gel in the column is then washed with 1,000 ml of 4.99M sodium chloride-containing 0.01M phosphate buffer solution. The results are summarized in Table 1.

TABLE 1

|  | Volume (ml) | Virus Content (CCA) | Protein Nitrogen Content* ($\mu$g/ml) | Recovery Rate of Virus (%) | Specific Activity | Degree of Purification |
| --- | --- | --- | --- | --- | --- | --- |
| Allantoic Fluid | 4,200 | 77 | 377.1 | 100.0 | 0.20 | 1.00 |
| Passed-through Solution | 6,700 | 1 | 209.2 | 2.1 |  |  |

TABLE 1-continued

|  | Volume (ml) | Virus Content (CCA) | Protein Nitrogen Content* (μg/ml) | Recovery Rate of Virus (%) | Specific Activity | Degree of Purification |
|---|---|---|---|---|---|---|
| Eluate | 170 | 1,797 | 448.0 | 94.5 | 4.01 | 20.05 |
| Washing Solution | 1,000 | 12 | 110.7 | 3.7 | 0.11 | 0.55 |

*By colorimetric analysis of substance precipitated with trichloro acetate.

As seen from the table, the influenza virus is substantially recovered into the eluate and the degree of purification (the specific activity of the eluate/ the specific activity of the starting allantoic fluid) is found to be 20.05.

EXAMPLE 2

The cellulose sulfate gel obtained in the manner as described in Preparation 2 is packed within a column (50 mmφ×70 mm), and the packed column is equilibrated with 0.04M sodium chloride-containing 0.01M phosphate buffer solution (pH 7.4). Then, through the column is passed 450 ml of an ether-treated vaccine solution, which has been obtained by refining B/Singapore type influenza virus and treating the virus with ether to remove lipids therin, by means of the above-mentioned conventional process, and contains HA and NA proteins as well as other proteins and nucleic acids. After the passage, the column is washed with 500 ml of 0.01M phosphate buffer solution containing 1.94M sodium chloride. The adsorbed material is then eluted with 0.01M phosphate buffer solution containing 4.99M sodium chloride, to give an eluate (130 ml). The gel is then elution-washed with 0.01M phosphate buffer solution containing 4.99M sodium chloride. The results are summarized in Table 2.

TABLE 2

|  | Volume (ml) | Virus Content (CCA) | Protein Nitrogen Content* (μg/ml) | Recovery Rate of Virus (%) | Specific Activity | Degree of Purification |
|---|---|---|---|---|---|---|
| Ether-treared Vaccine | 450 | 3,104 | 35.6 | 100.0 | 87.1 | 1.00 |
| Passed-through Solution | 950 | 216 | 10.1 | 14.7 | 21.4 | 0.25 |
| Eluate | 130 | 8,475 | 36.4 | 78.9 | 232.8 | 2.67 |
| Elution-washing Solution | 380 | 235 | 4.5 | 6.4 | 52.2 | 0.60 |

*By colorimetric analysis of substance precipitated with trichloro acetate.

As seen from the table, the degree of purification with the gel is about 2.7. Analysis of the eluate by means of single radial immunodiffusion shows that the eluate contains high amounts of HA and NA proteins.

EXAMPLE 3

The crosslinked dextran sulfate gel prepared in the manner as described in Preparation 3 is packed within a column (25 mmφ×100 mm), and the packed column is equilibrated with 0.14M sodium chloride-containing 0.01M phospate buffer solution (pH 7.4). Through the column is passed 50 ml of an allantoic fluid infected with A/Kumamoto ($H_1N_1$) type influenza virus. After the passage, the column is washed with 100 ml of 0.14M sodium chloride-containing 0.01M buffer solution, followed by elution with 1.49M sodium chloride-containing 0.01M phosphate buffer solution to obtain an eluate of 30 ml. The gel is then subjected to an elution-washing with 0.01M phosphate buffer solution containing 4.99M sodium chloride. The results are shown in Table 3.

TABLE 3

|  | Volume (ml) | Virus Content (CCA) | Protein Nitrogen Content* (μg/ml) | Recovery Rate of Virus (%) | Specific Activity | Degree of Purification |
|---|---|---|---|---|---|---|
| Allantoic Fluid | 50 | 218 | 75.0 | 100.0 | 2.91 | 1.00 |
| Passed-through Solution | 100 | 9 | 26.8 | 8.3 | 0.34 | 0.12 |
| Eluate | 30 | 313 | 17.8 | 86.1 | 16.35 | 5.62 |
| Elution-washing Solution | 50 | 12 | 10.8 | 5.5 | 1.11 | 0.38 |

*By colorimetric analysis of substance precipitated with trichloro acetate.

EXAMPLE 4

The crosslinked agarose sulfate gel parpared in the manner as described in Preparation 5 is packed within a column (25 mmφ×100 mm), and the packed column is equilibrated with 0.14M sodium chloride-containing 0.01M phosphate buffer solution (pH 7.4). Through the column is passed 150 ml of an allantoic fluid infected with A/Ishikawa ($H_3N_2$)type influenza virus. After the passage, the column is subjected to washing and elution treatments, as in Example 3, to give an eluate (50 ml). The gel is then subjected to an elution-washing with 0.01M phosphate buffer solution containing 4.99M sodium chloride. The results are shown in Table 4.

TABLE 4

| | Volume (ml) | Virus Content (CCA) | Protein Nitrogen Content* (μg/ml) | Recovery Rate of Virus (%) | Specific Activity | Degree of Purification |
|---|---|---|---|---|---|---|
| Allantoic Fluid | 150 | 22 | 47.2 | 100.0 | 0.47 | 1.00 |
| Passed-through Solution | 250 | 1 | 22.1 | 7.6 | 0.05 | 0.11 |
| Eluate | 50 | 55 | 9.8 | 83.3 | 5.61 | 11.94 |
| Elution-washing Solution | 100 | 3 | 10.7 | 9.1 | 0.28 | 0.60 |

*By colorimetric analysis of substance precipitated with trichloro acetate.

EXAMPLE 5

The cellulose sulfate gel prepared in the manner as described in Preparation 2 is packed within a column (50 mmϕ×70 mm), and the packed column is equilibrated with 0.14M sodium chloride-containing 0.01M phosphate buffer solution (pH 7.4). Through the column is passed 300 ml of an allantoic fluid infected with A/Miami ($H_3N_6$) type equine influenza virus. After the passage, the column is washed, followed by elution with 0.14M sodium chloride-containing 0.01M phosphate buffer solution to obtain an eluate of 50 ml. The gel is then subjected to an elution-washing with 0.01M phosphate buffer solution containing 4.99M sodium chloride. The results are shown in Table 5.

TABLE 5

| | Volume (ml) | Virus Content (CCA) | Protein Nitrogen Content* (μg/ml) | Recovery Rate of Virus (%) | Specific Activity | Degree of Purification |
|---|---|---|---|---|---|---|
| Allantoic Fluid | 300 | 40 | 45.8 | 100.0 | 0.87 | 1.00 |
| Passed-through Solution | 500 | ·2 | 15.8 | 8.3 | 0.13 | 0.15 |
| Eluate | 50 | 197 | 21.5 | 82.1 | 9.16 | 10.53 |
| Elution-washing Solution | 200 | 7 | 12.3 | 11.7 | 0.57 | 0.66 |

*By colorimetric analysis of substance precipitated with trichloro acetate.

What is claimed is:

1. A method for the purification of an influenza virus, which comprises subjecting a solution containing the influenza virus to column chromatography using, as a gel for chromatography, a sulfuric acid ester of cellulose or a crosslinked polysaccharide, said sulfuric acid ester being prepared by treating a gel of cellulose or crosslinked polysaccharide with a sulfating agent in an organic solvent.

2. The method as claimed in claim 1, wherein the influenza virus-containing solution is an allantoic solution infected with the influenza virus.

3. The method as claimed in claim 1, wherein the influenza virus-containing solution is one which has been subjected to pretreatment including a treatment with ether to remove lipids.

4. The method as claimed in of claim 1, wherein the sulfuric acid ester of a crosslinked poly-saccharide is selected from the group consisting of a cross-linked cellulose sulfate, a crosslinked agarose sulfate and a crosslinked dextran sulfate.

5. The method as claimed in claim 1, wherein the sulfuric acid ester of cellulose is a sulfuric acid ester of crystalline cellulose or a cellulose having a crystalline area and non-crystalline area.

* * * * *